United States Patent [19]
Shi et al.

[11] Patent Number: 6,004,943
[45] Date of Patent: Dec. 21, 1999

[54] PROTEIN-COATED MEDICAL SUBSTRATES FOR LOCAL DELIVERY OF GENES AND METHOD OF FORMING COATINGS ON THE SUBSTRATES

[75] Inventors: Rui-wen Shi, Tianjin; Run-lin Gao, Beijing, both of China

[73] Assignees: Inst. of Biomedical Engineering, Chinese Acdmy of Med. Science, Tianjin; Cardiovascular Inst. of Fu Wai Hospital, Chinese Acdmy of Med. Science, Beijing, both of China

[21] Appl. No.: 08/753,523

[22] Filed: Nov. 26, 1996

[30] Foreign Application Priority Data

Nov. 27, 1995 [CN] China ................................. 95118371

[51] Int. Cl.$^6$ ........................................ A61K 48/00
[52] U.S. Cl. ............................ 514/44; 424/428; 427/2.1; 604/53; 435/455; 435/320.1; 530/354; 530/356; 623/1
[58] Field of Search .................... 514/44; 935/53, 935/55, 60; 530/354, 356; 536/23.1; 427/2.1; 623/1; 428/305.5, 483; 435/455, 458, 320.1; 424/428

[56] References Cited

U.S. PATENT DOCUMENTS

| | | | |
|---|---|---|---|
| 4,167,045 | 9/1979 | Sawyer | 427/2.1 |
| 4,373,009 | 2/1983 | Winn | 424/428 |
| 4,452,925 | 6/1984 | Kuzma et al. | 523/106 |
| 5,091,205 | 2/1992 | Fan | 427/2.1 |
| 5,328,955 | 7/1994 | Rhee et al. | 525/54.1 |
| 5,451,453 | 9/1995 | Gagnon et al. | 428/305.5 |
| 5,487,895 | 1/1996 | Dapper et al. | 424/278.1 |
| 5,529,914 | 6/1996 | Hubbell et al. | 435/182 |
| 5,584,875 | 12/1996 | Duhamel et al. | 623/1 |
| 5,591,227 | 1/1997 | Dinh et al. | 623/1 |
| 5,643,580 | 7/1997 | Subramaniam | 424/400 |
| 5,643,681 | 7/1997 | Voorhees et al. | 428/483 |
| 5,652,225 | 7/1997 | Isner | 514/44 |
| 5,693,085 | 12/1997 | Buirge et al. | 623/1 |
| 5,763,416 | 6/1998 | Bonadio et al. | 514/44 |
| 5,769,883 | 6/1998 | Buscemi et al. | 623/1 |

FOREIGN PATENT DOCUMENTS

| | | |
|---|---|---|
| WO 89/10377 | 11/1989 | WIPO . |
| WO 95/24929 | 9/1995 | WIPO . |
| WO 97/46268 | 12/1997 | WIPO . |
| WO 97/46590 | 12/1997 | WIPO . |

OTHER PUBLICATIONS

"Local drug delivery devices for use in the vasculature," Huens, *The Lancet,* vol. 347, n. 9002, p. 679, Mar. 9, 1996.
Wilensky et al. Trends Cardiovasc Med 1993; 3:163–170.

*Primary Examiner*—Scott D. Priebe
*Assistant Examiner*—Dave Trong Nguyen
*Attorney, Agent, or Firm*—Pennie & Edmonds LLP

[57] ABSTRACT

This invention is directed to an article, such as a medical device, for local delivery of genes. The article comprises a substrate coated with a cross-linked protein. The invention is also directed to a method for coating an article with cross-linked protein. An additive may be optionally incorporated into the coating. The crosslinked protein coating can strongly absorb genes. Thus, the coated article can be used to locally deliver genes to a target site. The coating of the invention exhibits excellent biocompatibility and biodegradability, and does not cause toxicity or side-effects.

13 Claims, No Drawings

PROTEIN-COATED MEDICAL SUBSTRATES FOR LOCAL DELIVERY OF GENES AND METHOD OF FORMING COATINGS ON THE SUBSTRATES

This application claims priority to Chinese patent application 95118371.0, filed Nov. 27, 1995.

TECHNICAL FIELD

This invention relates to coated substrates and the method of forming the coatings. The invention more particularly relates to protein coated articles, such as medical devices, which are used for the local delivery of genes.

BACKGROUND ART

Due to advances in molecular biology, the pathologenesis of many diseases can be elucidated at the gene level. This makes it possible to provide accurate diagnosis and effective treatment of such diseases. In fact, the treatment of many diseases, such as cardiovascular diseases, cerebral diseases, tumor, diabetes, AIDS, and gene therapy is attracting more and more attention. For example, if an anti-thrombogenic gene is delivered and localized to a specific artery, highly efficient gene transfer to the vascular cells and transgene expression at the target site will occur, effecting suppression of thrombosis. However, a key problem of localized delivery of exogenous genes within the body, so far, has not been solved. Simons et al. employed Pluronic F127 gel as a vehicle for gene delivery and localization (1992, *Nature* 359(3):67–70). A gene was added to a gel and then delivered to the carotid artery of an animal. A shortcoming of this method is that the gel is susceptible to being flushed from the target site by blood flow. Therefore, localized delivery of the gene cannot be effectively achieved. With respect to coated substrates, although several methods have been disclosed, the objective of those inventions is to have hydrophilic coatings lubricate the articles when they a:re in contact with an aqueous-based medium, such as a body fluid. The lubricous surface can decrease injury to macous membranes and other body tissue caused by the presence of the articles. U.S. Pat. No. 4,373,009 discloses a hydrophilic coating. The disclosed coating material is vinyl pyrrolidone copolymer containing active hydrogen. Another hydrophilic coating is made from polyacrylates. This coating is described by You-link Fan in U.S. Pat. No. 5,091,205. These types of coatings can exhibit low coefficient of friction when in contact with aqueous-based medium. But they are not fit for local delivery of genes because they do not absorb genes strongly enough. In addition, these polymers have unknown quality with respect to biocompatibility, purity, and toxicity. Thus, there remains a distinct need for a vehicle that can absorb genes strongly, and thereby locally deliver genes.

SUMMARY OF THE INVENTION

The present invention is directed to coated substrates having a cross-linked protein coating which can strongly absorb genes, and thereby used to deliver genes to the desired target site., This invention is also directed to a method for coating the substrates. The coatings provided by this invention are formed by contacting substrates with a protein dissolved in a solvent. The protein is then cross-linked by chemical methods, such as reaction with a chemical cross-linker, or physical methods, such as high energy radiation. The coatings adhere to the substrates strongly and the coated substrate can be implanted at the target site of the body. Furthermore, the coatings provided by this invention exhibit excellent biocompatibility and biodegradability, and do not evoke toxicity and/or side-effects.

DETAILED DESCRIPTION OF THE INVENTION

The coatings provided by this invention are made from proteins each having a molecular weight greater than 10,000 daltons. The protein is cross-linked and one or more additives may be incorporated into the coating. In the method provided by the invention, the coatings are formed by contacting substrates with a protein solution which may contain one or more additives or no additive. The concentration of the protein in the solution is in the range of 0.1% to 40%, and that of additives is in the range of 0% to 30%. A wide variety of proteins can be employed in preparing the coatings, including, but not limited to proteins of soft or hard tissues of animals or human beings; e.g., gelatin, collagen, albumin, and the like. The preferred protein is gelatin. Any applying solvent which can dissolve the protein may be used to prepare the protein solution. However, different applying solvents are preferred for applying protein coatings to different substrates. If desired, a mixture of applying solvents may be used. The typical solvents are water, glycerin, N,N-dimethylformamide (DMF), and dimethylsulfoxide (DMSO). For some special purposes, it may be desirable to incorporate one or more additives in the coatings. For some of the substrates comprising flexible rubber or plastics, a coating which contains a plasticizer is preferred so as to minimize the loss of flexibility of the substrate. A variety of plasticizers such as glycerin, esters of fatty acids, and the like can be employed. Other additives can also be incorporated into the coatings. Examples include surfactants, water-soluble drugs, biological agents, antimicrobial agents, and the like. Surfactants can improve the spreading property of the protein solution of the substrate. Useful surfactants include: cationic surfactants, such as alkyl quaternary ammonium salts; anionic surfactants, such as sodium dodecyl sulfate; and non-ionic surfactants, such as poly (oxyethylene sorbitan monooleate). If the substrate is a device which is inserted into a blood vessel, such as an intravascular stent, a catheter, or an angioplasty balloon, it may be desirable to have as an additive a thrombogenic agent such as heparin. Additives which are anti-microbial agents such as sodium benzoate, can prevent bacterial growth on or around the substrate. The additives incorporated in the coating must, of course, be compatible with the components of the coatings and have no undesirable biological properties which would limit their use.

The process of coating a substrate is as follows:

1. Preparation of Protein Solution

A protein or a mixture of two or more proteins are dissolved in a solvent. The concentration of protein solution is from 0.1% to 40%, preferably from 0.5% to 30%. If desired, an additive may be added after dissolving the protein. The additive concentration is controlled in the range of 0% to 3.0% based on total weight of protein solution.

2. Cross-linking of Protein Coating

Either a chemical cross-linker or high energy radiation can be employed to cross-link the protein. In the case of chemical crosslinking, the protein solution firstly contacts with the substrate, then the crosslinker is applied to the protein solution, or the crosslinker can be added to the protein solution before the solution is applied to the substrate. The chemical crosslinker can be selected from a wide variety of compounds, including aldehyde compounds, such as formaldehyde, acetaldehyde, glutaraldehyde; ketone compounds such as butanedione, hexanedione; isocyanate compounds such as 2,4-toluene diisocyanate, 4,4'-diphenylmethane diisocyanate, 1,6-hexamethylene diisocyanate, p,p',p''triphenylmethane triisocyanate, polymethylene polyisocyanate; epoxy compounds such as epichlorohydrin, and the like. The amount of crosslinker should be controlled within the range of 0.01 to 10 grams, preferably 0.1 to 5 grams (based on 100% content) per 100 grams of protein. In the case of high energy radiation crosslinking, high doses of radiation produced by a variety of sources can be employed. Typical radiation is $\tau$-rays produced by $Co^{60}$.

3. Coating Substrate with Protein Solution

The technique employed in coating the substrate is not necessarily critical, and any method suitable for making a thin coating may be adopted. These include, but are not limited to, dipping, spraying, painting and the like. The substrate may form any desired shape, size, or configuration. They include a wide variety of articles, such as medical devices. Example medical devices are metallic intravascular stent, catheter, guidewire, angioplasty balloon, polymeric stent, artificial blood vessel, sheath, bone nail, artificial joint, splint and the like. The substrate may be made from any material including metal, polymer, bone, and ceramic material. Examples of metals that may be used as substrate are stainless steel, tantalum, titanium, memory alloy and the like. Examples of polymers that may be used as substrate are polyethylene, polyvinylchloride, polyurethane, poly(ethylene terephthalate), poly(butylene terephthalate), polyamide, polystyrene, polycarbonate, polycaprolactone, polylactide, polyglycolide, polydioxanone and related copolymers. Alternatively, the substrate may be an article already having a coating. Such coatings may comprise any material, such as polyurethane, polyisocyanate, the reaction products of isocyanates and polyols, isocyanate monomers, epoxy resin, and compounds containing active groups including —OH (hydroxyl), —SH (sulfhydral), —NH$_2$ (amino), —NH(imino), —COHN$_2$ (carbonamide), —O— (epoxy), and =O(aldo).

4. Drying of the Coating

Either air drying or oven drying can be employed to remove the solvent of the coating solution. A shorter period is needed when dried at an elevated temperature. Preferably, the drying temperature is controlled within the range of 4° C. to 100° C. The drying period can range from 0.3 hours to 100 hours. The higher the drying temperature, the shorter the drying time needed.

5. Controlling of Coating Thickness

Coating thickness can be controlled by changing the concentration of the protein solution and the number of coating applied. The lower the protein concentration, the thinner is the coating. If desired, a thicker coating can be obtained by repeating the coating process. Generally, coating thickness may range from 0.1 to 100 microns, preferably from 1 to 20 microns.

In contrast with the prior art, the instant invention provides entirely novel coated substrates which can act as vehicles for the local delivery of genes. The protein coatings disclosed in the instant invention can strongly absorb genes because protein is the expression product of genes, and a large number of hydrogen bonds may be formed between protein molecules and genes. Further, the protein coatings are hydrophilic, and therefore have strong affinity with water-soluble agents, such as genes. The proteins used in this invention originate from the body tissue of animals or human beings, and therefore, the resultant coatings exhibit excellent biocompatibility and biodegradability. Moreover, due to crosslinking, the protein coatings are stable so that they can not be flushed out. The combination of these properties is not available from other prior art coated substrates. Thus, the instant invention provides an ideal method for the local delivery of genes.

EXAMPLE 1

1.0 gram glycerin and 0.5 milliliters 37% (weight/weight) solution of formaldehyde in water were added with mixing to 100 milliliters 10% solution of gelatin in water. A stainless steel intravascular stent was dipped into this mixture for 10 seconds, removed from the mixture, and air dried at 20° C. for 20 hours. The finished coating was firm and flexible. The coated stent was soaked in high-titer Ad-β gal viral stock for 1 minute, and then was implanted into the femoral arteries of dog and mini-pig. The animals were sacrificed after 7 days and the experimental artery segments were assayed for gene expression by X-gal staining. It was surprisingly found that a large number of cell nuclei in the sub-intima, media, and adventitia was stained by dark blue. This demonstrated high efficient gene transfer. The control experiment was carried out using a stent without the coating. No blue staining was observed. These results suggest that the protein coated stent can locally deliver genes successfully.

EXAMPLES 2 to 22

Additional experiments were conducted to evaluate various substrates or articles coated in accordance with the present invention. Variations were made in the substrate, coating composition, crosslinker, drying condition, number of coating, and method of coating used. The pertinent data are set forth in Table 1 below. Identical results with that of Example 1 were obtained.

EXAMPLE 23

1.0 gram glycerin was added to 100 milliliters 10% solution of gelatin in water. The mixture was blended for 5 minutes using an electromagnetic mixer. A stainless steel plate was soaked in this mixture for 30 seconds, removed, and air-dried at 20° C. for 10 hours. The coated stainless steel plate was dipped in a 10% solution of formaldehyde in water for 1 minute, then air-dried at 20° C. for 40 hours. The result of gene transfer was the same as that of Example 1.

EXAMPLE 24

1.0 gram glycerin and 15 milligrams sodium dodecyl sulfate were added to 100 milliliters 10% solution of gelatin in water, the mixture was blended for 5 minutes using an electromagnetic mixer. A poly(ethylene terephthalate) plate was immersed in this mixture for 1 minute, removed from the mixture, and irradiated with 3.0 Mrad $Co^{60}$ $\tau$-rays. The coated plate was dried at 20° C. for 10 hours. The result of gene transfer was identified with that of Example 1.

TABLE 1

Pertinent Data to the Embodiment of Examples 2–22

| example No. | substrate | protein solution Substances (protein + solvent) | (%) | crosslinker solution substance | (%) | additives substances | (g) | drying condition t (° C.) | hours | times of coating (method) |
|---|---|---|---|---|---|---|---|---|---|---|
| 2 | stainless steel plate | gelatin + water | 5 | formaldehyde | 0.30 | — | — | 20 | 24 | 1 (painting) |
| 3 | stainless steel plate | gelatin + DMS* | 2 | TDI* | 0.40 | — | — | 60<br>20 | 1.5<br>48 | 2 (soaking) |
| 4 | stainless steel plate | gelatin + water + DMS* | 6 | formaldehyde | 0.30 | glycerin | 1.0 | 60<br>20 | 1<br>48 | 2 (soaking) |
| 5 | stainless steel plate | gelatin + water | 10 | formaldehyde | 0.30 | heparin | 0.1 | 20 | 24 | 1 (painting) |
| 6 | stainless steel plate | gelatin + water | 10 | formaldehyde | 0.30 | S* | 0.015 | 20 | 24 | 1 (painting) |
| 7 | poly(ethylene terephthalate)membrane | gelatin + water | 10 | formaldehyde | 0.30 | glycerin<br>S | 1.0<br>0.015 | 20 | 40 | 1 (painting) |
| 8 | nylon-6 membrane | gelatin + water | 10 | formaldehyde | 0.30 | glycerin<br>S | 1.0<br>0.015 | 20 | 40 | 1 (painting) |
| 9 | angioplasty balloon (USC1) | gelatin + water | 5 | formaldehyde | 0.30 | glycerin<br>S | 0.7<br>0.015 | 20 | 40 | 1 (soaking) |
| 10 | angioplasty balloon (Cordis) | gelatin + water | 5 | formaldehyde | 0.30 | glycerin<br>S | 0.7<br>0.015 | 20 | 40 | 1 (soaking) |
| 11 | angioplasty balloon (cordis) | gelatin + water | 5 | formaldehyde | 0.30 | glycerin | 1.0 | 20<br>20 | 0.2<br>20 | 2 (soaking) |
| 12 | stainless steel plate having isocyanate coating | gelatin + water | 10 | formaldehyde | 0.30 | glycerin | 1.0 | 20 | 48 | 1 (spraying) |
| 13 | poly(ethylene terephthalate) membrane having isocyanate coating | gelatin + water | 10 | formaldehyde | 0.30 | glycerin<br>S | 1.0<br>0.015 | 20 | 48 | 1 (spraying) |
| 14 | stainless steel artificial joint | gelatin + water | 5 | glutaral-dehyde | 0.15 | glycerin<br>TWEEN-80 | 0.7<br>0.1 | 20 | 48 | 1 (soaking) |
| 15 | polyurethane plate | gelatin + water | 5 | butanedione | 0.50 | glycerin<br>S | 0.7<br>0.020 | 20 | 24 | 1 (painting) |
| 16 | ceramic plate | gelatin + water | 4 | formaldehyde: glutaral dehyde (1:1) | 0.50 | glycerin<br>N* | 1.0<br>0.012 | 20 | 24 | 1 (painting) |
| 17 | stainless steel plate | bovine serum albumin + water | 5 | formaldehyde | 0.12 | glycerin<br>S | 0.6<br>0.014 | 20 | 24 | 1 (painting) |
| 18 | tantalum intravascular stent | gelatin + water | 5 | formaldehyde | 0.15 | glycerin<br>S | 0.4<br>0.014 | 20 | 40 | 1 (soaking) |
| 19 | titanium intravascular stent | gelatin + water | 5 | formaldehyde | 0.15 | glycerin<br>S | 0.4<br>0.014 | 20 | 40 | 1 (soaking) |
| 20 | memory alloy intravascular stent | gelatin + water | 5 | formaldehyde | 0.15 | glycerin<br>S | 0.4<br>0.014 | 20 | 40 | 1 (soaking) |
| 21 | stainless steel intravascular stent | gelatin + water | 10 | formaldehyde | 0.5 | glycerin | 1.0 | 30<br>20 | 0.5<br>40 | 2 (soaking) |
| 22 | stainless steel intravascular stent | collagen + water | 1 | formaldehyde | 0.5 | glycerin | 1.0 | 30<br>20 | 0.5<br>40 | 2 (soaking) |

*DMS—dimethylsulfoxide, TDI—2,4-toluene diisocyanate, S—sodium dodecyl sulfate, N—hexadecyl trimethyl ammonium bromide.

This invention is not to be limited by the embodiments described herein, which is given by way of examples and not of limitation, since many variations can be made by those skilled in the art without departing from the scope or spirit of the appended claims.

We claim:

1. An intravascular stent which is permanently implanted in the vessel lumen of a patient and which is used for locally delivering genes in a vessel comprising (a) a substrate, (b) a coating adhering to the substrate, and (c) a genetic material which is adsorbed to the surface of the coating, wherein the coating comprises a matrix of randomly interconnected protein molecules comprising one or more species of protein.

2. The intravascular stent of claim 1, wherein each species of protein has a molecular weight of greater than 10,000 daltons.

3. The intravascular stent of claim 1, wherein the substrate comprises a metal, polymer, bone, or ceramic.

4. The intravascular stent of claim 3, wherein the metal is stainless steel, tantalum, titanium, or memory alloy.

5. The intravascular stent of claim 3, wherein the polymer is polyethylene, polyvinylchloride, polyurethane, poly (ethylene terephthalate), poly(butylene terephthalate), polyamide, polystyrene, polycarbonate, polycarprolactone, polylactide, polyglycolide, or polydioxanone.

6. The intravascular stent of claim 1, wherein the coating additionally comprises an additive.

7. The intravascular stent of claim 6, wherein the additive is a plasticizer.

8. The intravascular stent of claim 7, wherein the plasticizer is glycerin.

9. The intravascular stent of claim 6, wherein the additive is a biological agent.

10. The intravascular stent of claim 9, wherein the biological agent is heparin, an anti-thrombogenic agent, an anti-platelet agent, or an agent that inhibits smooth muscle cell proliferation.

11. The intravascular stent of claim 6, wherein the additive is a surfactant.

12. The intravascular stent of claim 2, wherein each species of protein is gelatin, collagen or albumin.

13. The intravascular stent of claim 1, wherein the one or more species of protein is gelatin.

* * * * *

UNITED STATES PATENT AND TRADEMARK OFFICE
CERTIFICATE OF CORRECTION

PATENT NO.     : 6,004,943
DATED          : December 21, 1999
INVENTOR(S)    : Rui-wen SHI et al.

It is certified that error appears in the above-identified patent and that said Letters Patent is hereby corrected as shown below:

Title page,
"[73] Assignees:", change "Inst. Of Biomedical Engineering, Chinese Acdmy of Med. Science" to --Institute of Biomedical Engineering, Chinese Academy of Medical Science -- and "Cardiovascular Inst. Of Fu Wai Hospital, Chinese Acdmy of Med. Science" to --Cardiovascular Institute & Fu Wai Hospital, Chinese Academy of Medical Science --.

Signed and Sealed this

Fourteenth Day of August, 2001

*Attest:*

*Attesting Officer*

NICHOLAS P. GODICI
*Acting Director of the United States Patent and Trademark Office*